US010561439B2

(12) United States Patent
Silvestro

(10) Patent No.: US 10,561,439 B2
(45) Date of Patent: *Feb. 18, 2020

(54) ANGIOPLASTY BALLOON HAVING SELECTIVELY DEPLOYABLE CUTTING OR SCORING ELEMENT AND RELATED METHODS

(71) Applicant: Invatec S.p.A, Roncadelle (IT)

(72) Inventor: Claudio Silvestro, Roncadelle (IT)

(73) Assignee: Invatec S.P.A, Roncadelle BS (IT)

( * ) Notice: Subject to any disclaimer, the term of this patent is extended or adjusted under 35 U.S.C. 154(b) by 249 days.

This patent is subject to a terminal disclaimer.

(21) Appl. No.: 15/729,180

(22) Filed: Oct. 10, 2017

(65) Prior Publication Data
US 2018/0028221 A1    Feb. 1, 2018

Related U.S. Application Data

(63) Continuation of application No. 13/870,613, filed on Apr. 25, 2013, now Pat. No. 9,808,276.

(51) Int. Cl.
| A61B 17/22 | (2006.01) |
| A61D 1/02 | (2006.01) |
| A61B 17/3207 | (2006.01) |
| A61M 25/10 | (2013.01) |

(52) U.S. Cl.
CPC ..... A61B 17/32075 (2013.01); A61M 25/104 (2013.01); *A61M 2025/109* (2013.01)

(58) Field of Classification Search
CPC .......... A61B 17/32075; A61M 25/104; A61M 2025/109

USPC ........................................................ 606/159
See application file for complete search history.

(56) References Cited

U.S. PATENT DOCUMENTS

| 4,745,919 A | 5/1988 | Bundy |
| 5,108,407 A | 4/1992 | Geremia et al. |
| 5,122,136 A | 6/1992 | Guglielmi et al. |
| 5,350,397 A | 9/1994 | Palermo et al. |
| 5,766,192 A | 6/1998 | Zacca |
| 6,113,622 A | 9/2000 | Hieshima |
| 6,203,547 B1 | 3/2001 | Nguyen et al. |
| 7,131,981 B2 | 11/2006 | Appling et al. |
| 7,396,358 B2 | 7/2008 | Appling et al. |
| 7,686,824 B2 | 3/2010 | Konstantino et al. |
| 7,708,755 B2 | 5/2010 | Davis, III et al. |
| 7,931,663 B2 | 4/2011 | Farnan et al. |

(Continued)

FOREIGN PATENT DOCUMENTS

| WO | WO2005/076833 | 8/2005 |
| WO | WO2006/124398 | 11/2006 |

(Continued)

OTHER PUBLICATIONS

PCT/US2014/032080, PCT International Search Report and The Written Opinion of the International Searching Authority, dated Aug. 21, 2014.

*Primary Examiner* — Amy R Weisberg

(57) ABSTRACT

Balloon angioplasty catheters having cutting or scoring members that are moveable in at least one direction between a stowed position (away from the angioplasty balloon) and an operative position (on the angioplasty balloon). A balloon catheter of the present invention alternately useable to perform balloon dilation of a body lumen with and without concurrent cutting or scoring.

20 Claims, 7 Drawing Sheets

(56) References Cited

U.S. PATENT DOCUMENTS

| | | | |
|---|---|---|---|
| 8,052,701 B1* | 11/2011 | Cox | A61B 17/320725 |
| | | | 606/159 |
| 2002/0029015 A1* | 3/2002 | Camenzind | A61B 17/22 |
| | | | 604/97.02 |
| 2002/0165569 A1 | 11/2002 | Ramzipoor et al. | |
| 2004/0034363 A1 | 2/2004 | Wilson et al. | |
| 2004/0193196 A1 | 9/2004 | Appling | |
| 2005/0021071 A1* | 1/2005 | Konstantino | A61B 17/320725 |
| | | | 606/194 |
| 2006/0074442 A1 | 4/2006 | Noriega | |
| 2006/0149308 A1* | 7/2006 | Melsheimer | A61B 17/320725 |
| | | | 606/192 |
| 2006/0173487 A1* | 8/2006 | Uflacker | A61B 17/320725 |
| | | | 606/198 |
| 2006/0276823 A1 | 12/2006 | Mitelberg et al. | |
| 2007/0073329 A1* | 3/2007 | Hardert | A61M 25/104 |
| | | | 606/192 |
| 2007/0093781 A1* | 4/2007 | Kugler | A61B 17/221 |
| | | | 604/510 |
| 2012/0022536 A1 | 1/2012 | Lualdi | |
| 2016/0095619 A1* | 4/2016 | McMahon | A61B 17/320725 |
| | | | 606/159 |

FOREIGN PATENT DOCUMENTS

| | | |
|---|---|---|
| WO | WO2009/046206 | 4/2009 |
| WO | WO2012/009409 | 1/2012 |
| WO | WO2012/009412 | 1/2012 |

* cited by examiner

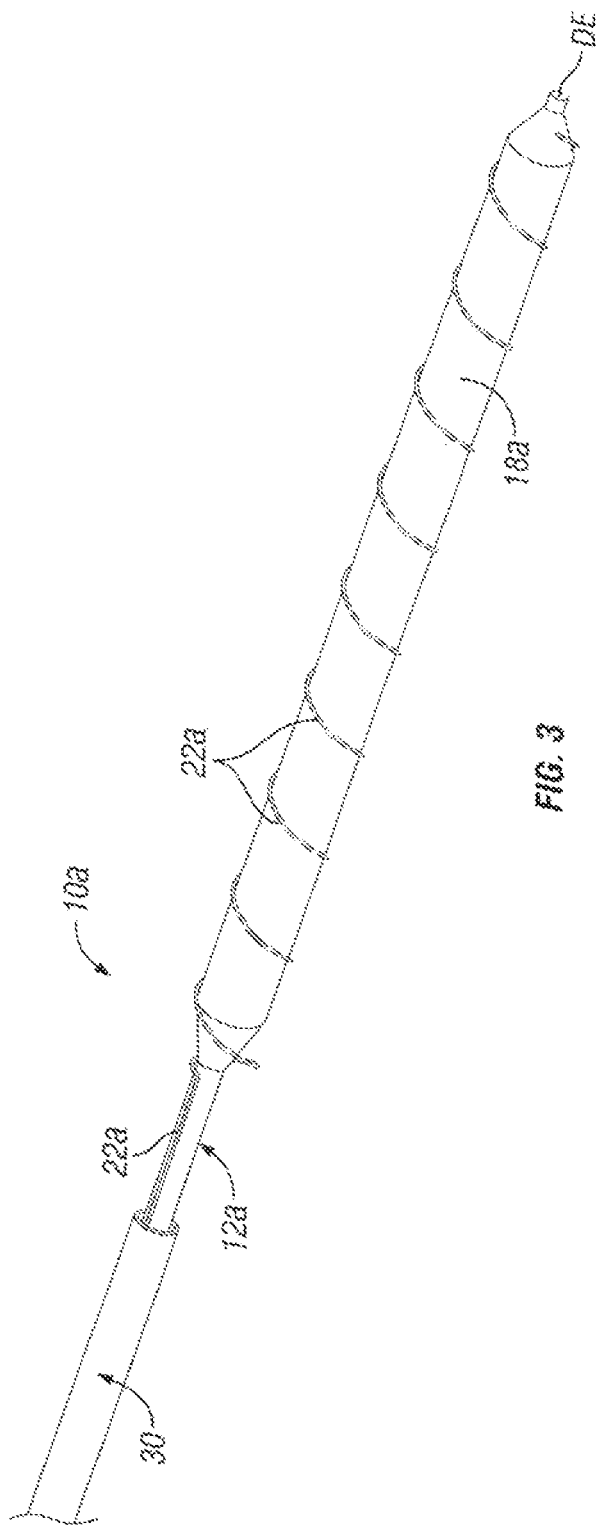

ANGIOPLASTY BALLOON HAVING SELECTIVELY DEPLOYABLE CUTTING OR SCORING ELEMENT AND RELATED METHODS

This application is a continuation of U.S. patent application Ser. No. 13/870,613, filed Apr. 25, 2013 and entitled, "ANGIOPLASTY BALLOON HAVING SELECTIVELY DEPLOYABLE CUTTING OR SCORING ELEMENT AND RELATED METHODS," the entire content of which is incorporated by reference herein.

FIELD OF THE INVENTION

The present invention relates to the fields of biomedical engineering and medicine and more particularly to devices and methods for treating atherosclerotic disease.

BACKGROUND OF THE INVENTION

Chronic occlusion of blood vessels caused by atherosclerotic plaque affects millions of patients worldwide. Percutaneous Transluminal Angioplasty (PTA) is the endovascular treatment of election for treating atherosclerotic plaque causing reduction of the vessel lumen patency, thus hindering physiological blood flow. PTA is performed by means of inflating a balloon that has been transluminally advanced into the lesion site by means of catheters. The inflated angioplasty balloon applies a radial pressure to the inner wall of the vessel in the area of the atherosclerotic lesion. This results in redistribution of the plaque to a more favorable configuration (i.e., one in which the stenosed region of the vessel lumen is widened thus allowing blood flow to be restored). PTA alone may, in some cases, bring about the desired stenosis reduction and restoration of physiological blood flow through the treated vessel.

However, in many cases, PTA performed using just a standard dilation balloon is not sufficient for achieving long-term patency of the diseased blood vessel. Sometimes the standard dilation balloon is unable to redistribute the plaque in the desired manner due to consistency of the plaque or other factors. Also, even in cases where the balloon dilation may initially bring about the desired redistribution of the plaque, subsequent restenosis or reocclusion can occur. To deal with this, balloon dilation is often accompanied by stenting of the lesion using bare metal or drug coated stents. One or more stents, when properly positioned, can provide physical scaffolding to hold the redistributed plaque in place and/or to otherwise deter subsequent narrowing of the vessel lumen. Drug coated stents additionally elute drugs which deter local inflammatory or other physiological processes which may contribute to restenosis or reocclusion.

Another clinical option emerged in the last years is represented by the use of drug-coated balloons (Drug-Eluting Balloons, DEB) according to which the outer surface of the angioplasty balloon is coated with drugs characterized by antiproliferative properties, inhibiting restenosis of the vessel. Stenting and DEB themselves, though, are not perfect. Reocclusion still happens at a much too high rate. Both stenting and drug-eluting balloon treatment generally need an adequate pre-treatment of the vessel lumen. The preliminary plaque dilatation provided by balloon angioplasty has to be properly managed, in order to best prepare the lesion for the following treatment (DEB and/or stenting). An adequate preliminary erosion of the plaque can reduce the risk of restenosis after stenting or DEB treatment. Therefore, lesion pre-treatment by means of balloon angioplasty can be the key for long-term clinical success.

Also, in some cases, PTA using a standard balloon can cause unintended dissections, perforations or other types of damage to the blood vessel wall. This damage sometimes occurs due to poor elasticity of the diseased blood vessel wall. Such damage to the vessel wall can also result from mispositioning of the balloon during the procedure. Such mispositioning of the balloon may occur when a standard balloon is inflated within an atherosclerotic lesion that is fibrotic or of an angular shape, resulting in slippage of the balloon from the intended site of dilation.

Also, in some cases, PTA using a standard balloon can sometimes create non-uniform or uncontrolled tears in tissues of the vessel wall and/or vasospasm of the vessel wall.

At least some of the above-summarized problems may be overcome by the use of a cutting or scoring balloon as opposed to a standard angioplasty balloon. Generally, the presence of a cutting or scoring element on the outer surface of the balloon during the dilation causes specific, controlled scoring or cutting of the atherosclerotic plaque in combination with the balloon dilation. This may help to cause the plaque to be permanently redistributed in the desired manner and may avoid other problems such as balloon slippage, vessel dissection or perforation, non-uniform or uncontrolled tears and/or the occurrence of vasospasm due to excessive stretching or over-dilation of the vessel wall.

Cutting and scoring balloons of the prior art have had cutting blades (known as atherotomes) or scoring member(s) formed or affixed on the outer surface of the balloon. Thus, if a standard balloon is initially advanced to the intended site of a PTA intervention and the operator then makes a decision to use a cutting or scoring balloon for some or all of the procedure, it is then necessary for the operator to remove the PTA catheter having the standard balloon and replace it with another PTA catheter that has a cutting or scoring balloon. On the other hand, if the operator initially advances a cutting or scoring balloon to the site of the lesion but subsequently decides that a standard balloon would be a better option, the operator must then remove the PTA catheter having the cutting or scoring balloon and replace it with another PTA catheter that has a standard balloon.

SUMMARY OF THE INVENTION

The present invention provides a PTA balloon catheter and methods whereby a cutting or scoring element may alternately be placed in accordance with the present invention.

Further in accordance with the present invention, there is provided a balloon catheter device comprising an elongate shaft, an inflatable balloon positioned on the catheter shaft and a cutting or scoring element that is alternately moveable between a first position wherein it does not cause the balloon to perform a cutting or scoring function and a second position wherein it does cause the balloon to perform a cutting or scoring function. The cutting or scoring element may be moveable between a stowed position in which the cutting or scoring element does not extend over the outer surface of the balloon in a manner that would cause the cutting or scoring element to perform a scoring function upon inflation of the balloon and an operative position in which the cutting or scoring element does extend over at least a portion of the outer surface of the balloon in a manner that will cause the cutting or scoring element to perform a cutting or scoring function upon inflation of the balloon. In some embodiments, the cutting or scoring element may comprise an elongate member that is retractable to the stowed position and advanceable to the operative position. As it advances over the outer surface of the balloon the elongate member may assume a desired configuration such as a helical shape. In other embodiments, the cutting or scoring element may be of a substantially fixed shape (e.g., a solid or perforated tube having scoring or cutting projection(s) formed on its outer surface or elongate member(s) that have been wound, coiled or braided into a generally tubular construct having an outer surface that performs the cutting or scoring function) that moves between the stowed position and the operative position. In such embodiments, the catheter shaft may include pushing and/or pulling members which move the cutting or scoring element from the stowed position to the operative position and/or from the operative position to the stowed position.

Further in accordance with the present invention, there is provided a method for using a device of the foregoing character to treat a stenotic region of a body lumen. In such method, the catheter shaft is advanced to a position where the balloon is within the stenotic region of the body lumen and a determination is made whether it is desired to perform a particular balloon dilation with or without cutting or scoring. If it is desired to perform the particular balloon dilation with cutting or scoring, the method further comprises causing the cutting or scoring member to be positioned in the operative position over the balloon in the inflated condition. On the other hand, if it is desired to perform that particular balloon dilation without cutting or scoring, the method further comprises keeping the scoring member in the stowed position while inflating the balloon. Some procedures may involve only a single balloon inflation with or without cutting or scoring. In other procedures the balloon may be inflated/deflated a plurality of times and an operator may elect to cause or not cause cutting or scoring some, all or none of the inflations of the balloon.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

FIG. 3 is a perspective view of a distal portion of another embodiment of a PTA catheter of the present invention.

DETAILED DESCRIPTION AND EXAMPLES

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

The present invention relates to a PTA balloon catheter having a cutting or scoring element that is moveable in at least one direction between a stowed position wherein the balloon is useable as a standard PTA balloon and an operative position wherein the PTA balloon is useable as a cutting or scoring balloon.

In the past, several disadvantages have been associated with conventional cutting or scoring balloons having fixed cutting or scoring elements on the outer surface of the balloon. For example, the presence of the cutting or scoring element can require special apparatus or techniques to avoid damaging the walls of healthy vessels through which the catheter is advanced and withdrawn. In many cases, the decision to use a cutting or scoring balloon is only made after traditional angioplasty using a standard balloon has failed. In such cases, it has heretofore been necessary to remove the standard PTA catheter and thereafter insert and advance into position another PTA catheter that has a cutting or scoring balloon. The examples shown in the accompanying drawings and described below illustrate how the present invention minimizes or overcomes these problems associated with the use of cutting or scoring balloons of the prior art.

Figure 1:
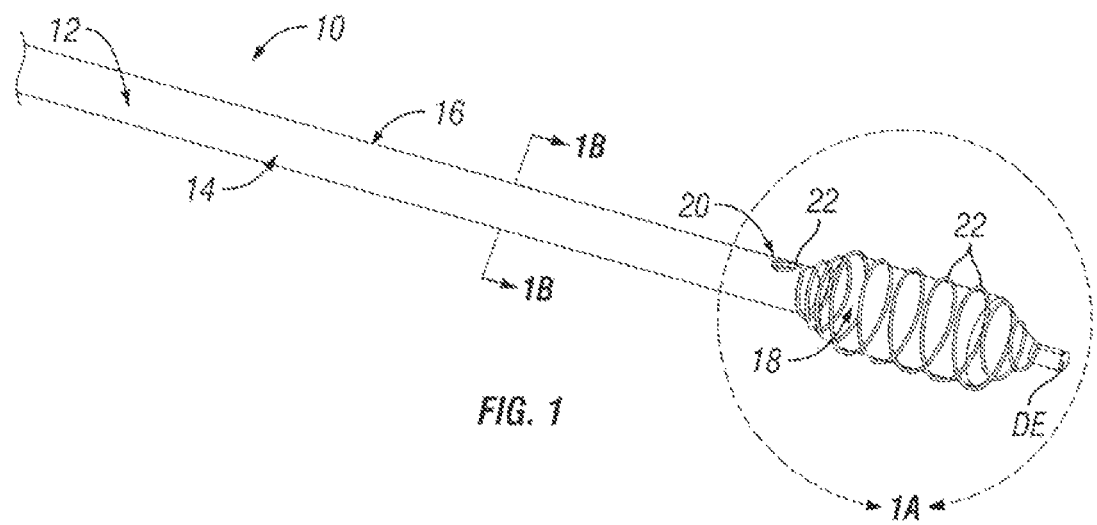
FIG. 1 is a perspective view of a distal portion of one embodiment of a PTA catheter of the present invention.
Figure 2A:
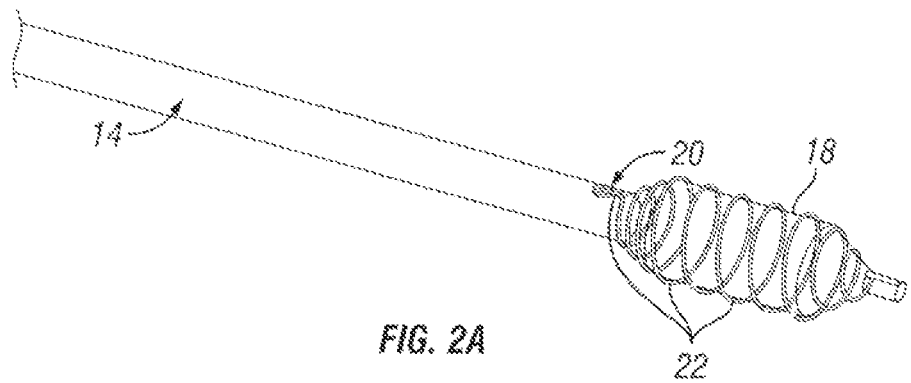
FIG. 2A shows the device of FIG. 1A with the cutting or scoring member in an operative position.
Figure 2B:
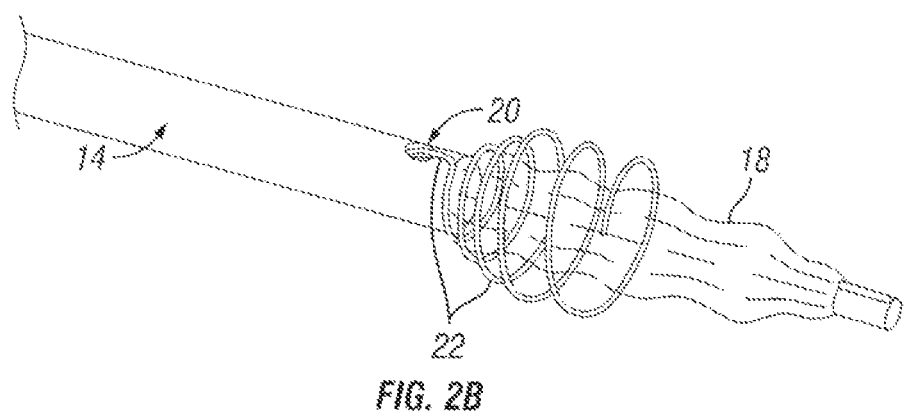
FIG. 2B shows the device of FIG. 2A with the cutting or scoring member in the process of being retracted from the operative position to a stowed position.
Figure 2C:
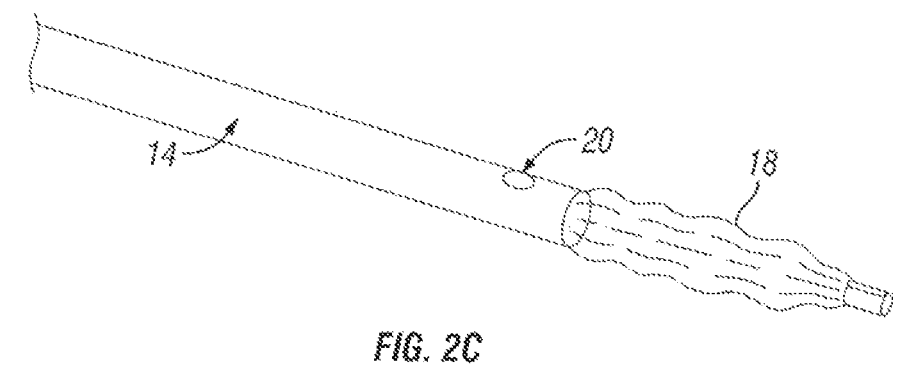
FIG. 2C shows the device of FIG. 2A after the cutting or scoring member has been fully retracted to its stowed position.

FIGS. 1 through 2C show a first embodiment of a PTA catheter device 10 of the present invention. This device 10 comprises an elongate, flexible catheter shaft 14 having a balloon 18 mounted on a distal portion thereof. In this example, the catheter shaft 14 comprises an outer tube 12 having a lumen 26 and an inner wall 16 that defines a second lumen 24. The second lumen 24 extends through the lumen 26 of outer tube 12 to an opening 20 formed in the side wall of the outer tube 12, proximal to the balloon 18. The inner wall 16 may comprise a second tube that is inserted through the lumen 26 of the outer tube 12 (i.e., tube within a tube construction) or, alternatively, the outer tube 12 may be a dual lumen tube (e.g. a dual lumen extrusion) such that the inner wall 16 comprises a bulkhead that separates lumen 26 from second lumen 24.

Figure 1A:
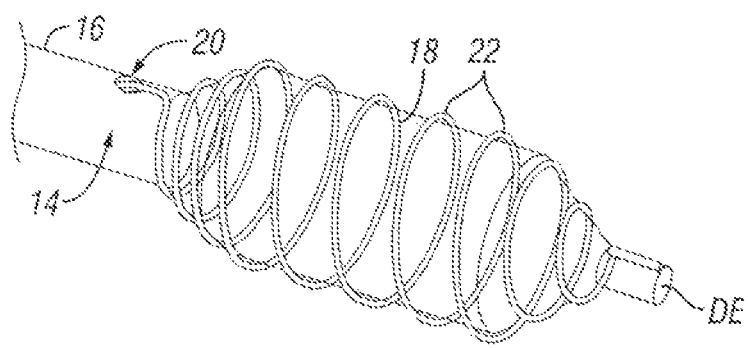
FIG. 1A is an enlarged view of Region 1A of FIG. 1.

The cutting or scoring member 22 is formed of an elastic or superelastic material, such as nickel-titanium alloy (Nitinol) and a distal portion of the cutting or scoring member 22 is preformed to a helically coiled configuration whereby it coils around the outer surface of the balloon 18 when the cutting or scoring member 22 is in an operative position as shown in FIGS. 1, 1A and 2A. In its stowed position, the cutting or scoring member 22 assumes a substantially straight configuration and is positioned within the second lumen 24. The cutting or scoring member 22 may have any suitable cross sectional configuration. In the particular example shown in the drawings, the cutting or scoring member 22 comprises a substantially round nickel-titanium alloy wire which, when in the operative position (FIGS. 1, 1A and 2A), causes helical scoring of atherosclerotic plaque in conjunction with inflation of the balloon 18 to dilate the lesion. Other alternative cross-sectional shapes (e.g., non-round wire, ribbon, etc.) and/or other alternative coiled configurations (other than the simple helix shown) may be employed. Also, more than one inner wall 16 and more than one cutting or scoring element 22 may be provided at differing radial locations on the main catheter shaft 14.

In one mode of use, the cutting or scoring member 22 may be initially placed in its operative position over the deflated balloon 18 and the distal tip of the scoring member 22 may be held in place or attached at the distal end DE by a releasable (e.g., breakable or separable) connection. The catheter shaft 12 is then advanced to the intended treatment site such that the deflated balloon is positioned within an atherosclerotic obstruction. The balloon 18 is then inflated to dilate the obstruction with a helical cut or score in the obstructive matter being concurrently formed by the operatively positioned cutting or scoring member 22 (FIG. 2A). By inflating and deflating the balloon 18 two or more consecutive times, it is possible to perform multiple plaque cutting or scoring treatments, if necessary.

After the desired cutting or scoring treatments have been performed, the balloon 18 may be deflated and any releasable distal attachment of the cutting or scoring member 22 is released. The cutting or scoring member 22 is then retracted proximally while the balloon 18 is in a deflated state (FIG. 2B) until it is fully in its stowed position within the secondary lumen 24 and away from the balloon 18 (FIG. 2C). Thereafter further inflation(s) of the balloon 18 may be performed at the original treatment site and/or other treatment sites, without cutting or scoring. In this manner, the same PTA catheter device 10 may be used to perform multiple PTA treatments with and/or without cutting or scoring of the obstructive matter. Use of this device 10 gives the operator the option, but not the necessity, of using the cutting or scoring member 22.

Figure 3A:
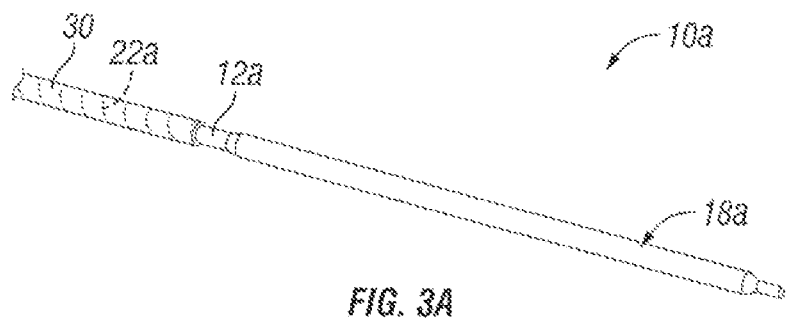
FIG. 3A shows the device of FIG. 3 with the cutting or scoring member on a stowed position and the balloon in a deflated configuration.
Figure 3B:
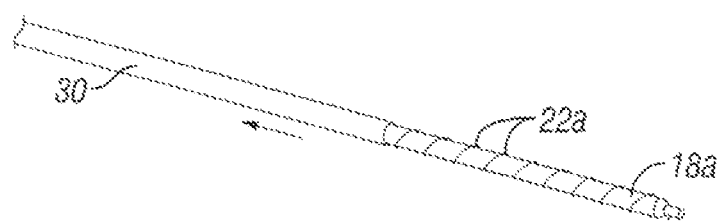
FIG. 3B shows the device of FIG. 3 with the cutting or scoring member fully advanced to its operative position while the balloon remains in a deflated configuration.
Figure 3C:
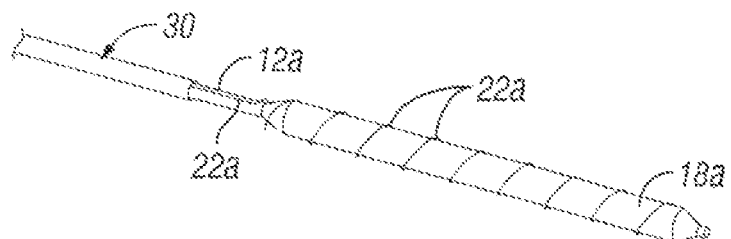
FIG. 3C shows the device of FIG. 3 with the cutting or scoring member fully advanced to its operative position and the balloon in an inflated configuration.

FIGS. 3 through 3C show a second embodiment of a PTA catheter device 10a of the present invention. In this embodiment, the device 10a comprises an elongate catheter 12a having a balloon 18a mounted on a distal segment of the catheter shaft 12a near its distal end DE. An advanceable/retractable outer sheath 30 is mounted around the catheter 12a and a cutting or scoring element 22a as described above extends along the exterior of the catheter shaft 12a, inside of the sheath 30. In the particular non-limiting example shown, a distal portion of the cutting or scoring member 22a is in the form of a linear helix having an inner diameter sized to allow it to advance over the balloon 18 when deflated. The cutting or scoring member 22a is initially in a stowed position on the catheter shaft 12a proximal to the balloon 18a and inside the outer sheath 30, as seen in FIG. 3A. In this manner, the outer sheath 30 covers and prevents the cutting or scoring member 22a from damaging blood vessel walls as the balloon 18 is advanced through the vasculature to the treatment site. With the cutting or scoring member 22a in this stowed position, the balloon 18a may be used to perform single/multiple traditional balloon angioplasty inflations at one or more treatment sites since it has no cutting or scoring element over it. Thereafter, if it is desired to perform one or more balloon inflations with concurrent cutting or scoring, the sheath 30 may be advanced in the distal direction over the deflated balloon 18a, bringing the cutting or scoring member 22a along with it, causing the cutting or scoring member 22a to be positioned on the deflated balloon 18a. Thereafter, the sheath 30 may be retracted proximally to expose the deflated balloon 18 with the cutting or scoring member 22a on it, as seen in FIG. 3B. Then, the balloon 18a may be inflated which causes the cutting or scoring member 22a to radially expand along with the balloon 18a, as shown in FIG. 3C. In this manner, balloon dilation with cutting or scoring of the obstructive matter may be accomplished. When the procedure is completed, the sheath 30 may be re-advanced over the deflated balloon 18a and the cutting or scoring member 22a, and the entire device 10a is then removed from the vasculature. Alternatively, when the procedure is completed, the outer sheath 30 may be re-advanced over the deflated balloon 18a and the cutting or scoring member 22a. Thanks to mechanical interference, the outer sheath 30 is able to capture the cutting or scoring member 22a so that the outer sheath 30 with the associated cutting or scoring member 22a may be removed proximally. In so doing, after the cutting/scoring process step, the balloon 18a may be used for successive dilatations of the stenotic lesion. Alternatively, the scoring member retrieval may also be supported by pulling the scoring member from its operative position, back inside the outer sheath 30. Additional components and/or design attributes may be added to the device 10a to facilitate the desired movement and deposition of the cutting or scoring member 22a on the balloon.

FIGS. 4A through 4E show another embodiment of a PTA device 10b of the present invention. This device 10b comprises an elongate inner catheter shaft 12b, a tubular outer catheter shaft 34 positioned around the inner shaft 12b and an outer sheath 36 positioned around the outer catheter shaft 34. An angioplasty balloon 18b is mounted on a distal portion of the inner catheter shaft 12b near its distal end DE. A cutting or scoring member 22b is initially positioned in a stowed position on the outer catheter shaft 34 between a proximal positioning balloon 38 and a distal positioning balloon 40. In this non-limiting example, the cutting or scoring element 22b comprises a wire helix with ring members 23 at either end. Such ring members 23 may also optionally be present on the ends of the cutting or scoring member 22 of the second embodiment of the device 10a shown in FIGS. 3 through 3D to deter the ends of the helical wire from damaging or perforating the balloon 18a. A control wire 41 is attached to the proximal ring member 23 of the cutting or scoring element 22b. Such control wire 41 extends along side the outer catheter shaft 34 through the lumen of the outer sheath 36, as may be appreciated from the showing of FIG. 4A.

Figure 4A:
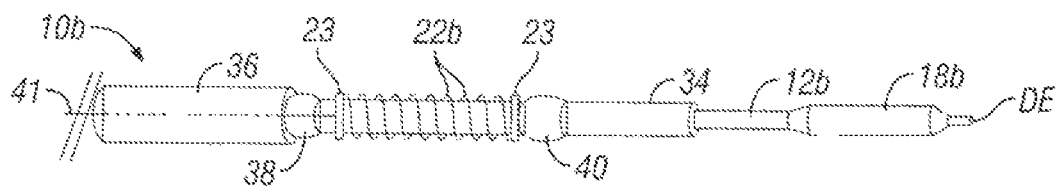
FIG. 4A shows another embodiment of a PTA catheter of the present invention with its cutting or scoring element in a stowed position and its balloon in a deflated configuration.
Figure 4B:
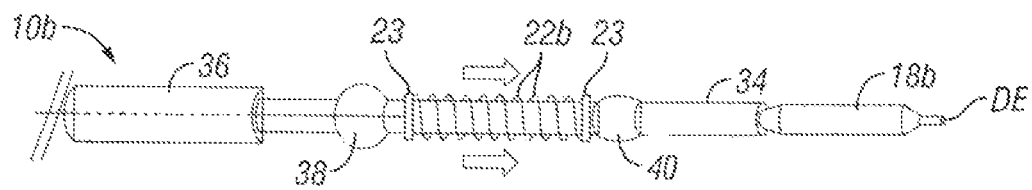
FIG. 4B shows the device of FIG. 4A during the process of advancing the cutting or scoring element from the stowed position to an operative position while the balloon remains in a deflated configuration.
Figure 4C:
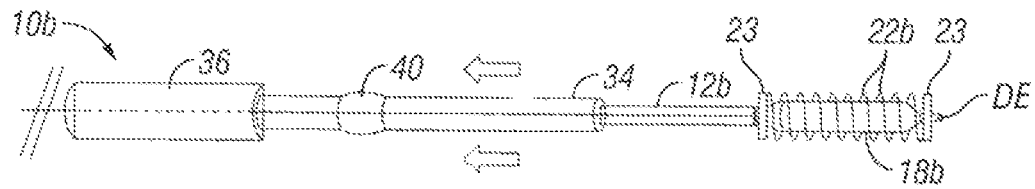
FIG. 4C shows the device of FIG. 4A with its cutting or scoring element fully advanced to the operative position while the balloon remains in a deflated configuration.
Figure 4D:
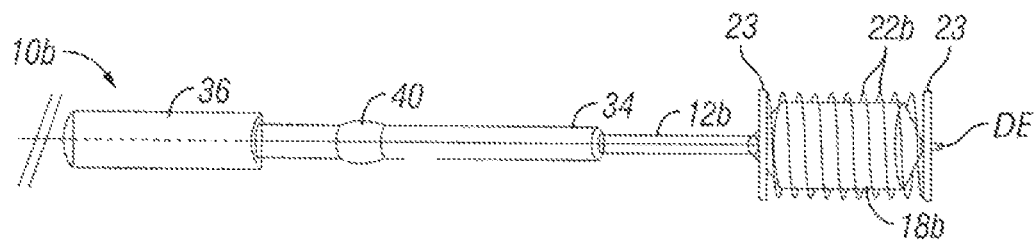
FIG. 4D shows the device of FIG. 4A with its cutting or scoring element fully advanced to the operative position and its balloon in an inflated configuration.
Figure 4E:
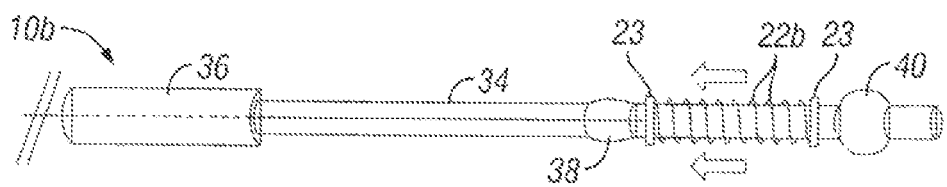
FIG. 4E shows the device of FIG. 4A during the process of retracting the cutting or scoring element from the operative position to the stowed position with the balloon in a deflated configuration.

With the cutting or scoring member 22b in the stowed position shown in FIG. 4A, the angioplasty balloon 18b may initially be used to perform (or attempt to perform) one or more standard balloon dilations without cutting or scoring. Thereafter, if it is desired to perform further balloon dilation(s) with concurrent cutting or scoring, the cutting or scoring member 22b may be moved from the stowed position (FIG. 4A) to an operative position on the angioplasty balloon 18b (FIGS. 4C and 4D). To accomplish this, the outer catheter shaft 34 may be advanced distally with the proximal positioning balloon 38 inflated and the distal positioning balloon 40 deflated as shown in FIG. 4B. The outer catheter shaft 34 is advanced in this manner to a position where the cutting or scoring member 22b is positioned over the deflated angioplasty balloon 18b. The control wire 41 is sufficiently rigid that, when the control wire 41 is held stationary, it deters not only distal movement, but also proximal movement, of the cutting or scoring member 22b. Thus, with the control wire 41 held stationary and the distal positioning balloon 40 deflated, the outer catheter shaft 34 is then retracted proximally, leaving the cutting or scoring member 22b on the deflated balloon 18b as shown in FIG. 4C. At a lesion to be treated, the angioplasty balloon 18b may then be inflated causing the cutting or scoring member 22b to radially expand along with radial enlargement of the inflating angioplasty balloon 18b, in the manner seen in FIG. 4D. This results in cutting or scoring of the obstructive matter concurrently with the exertion of outward dilating force by the inflated angioplasty balloon 18b. The angioplasty balloon 18b may then be deflated and re-inflated a desired number of times at a desire number of locations where cutting of scoring treatment is desired.

After the desired numbers of cutting or scoring treatments have been accomplished, if no further treatment is to be performed, the device 10b may be removed from the vasculature. Therefore, the balloon 18b is deflated and the cutting or scoring member 22b may be moved back to its stowed position on the outer catheter shaft 34. This may be accomplished by inflating the distal positioning balloon 40 and thereafter proximally advancing the outer catheter shaft 34 and/or proximally retracting the control wire 41 to cause the cutting or scoring member 22b to move to its stowed position.

Figure 5A:
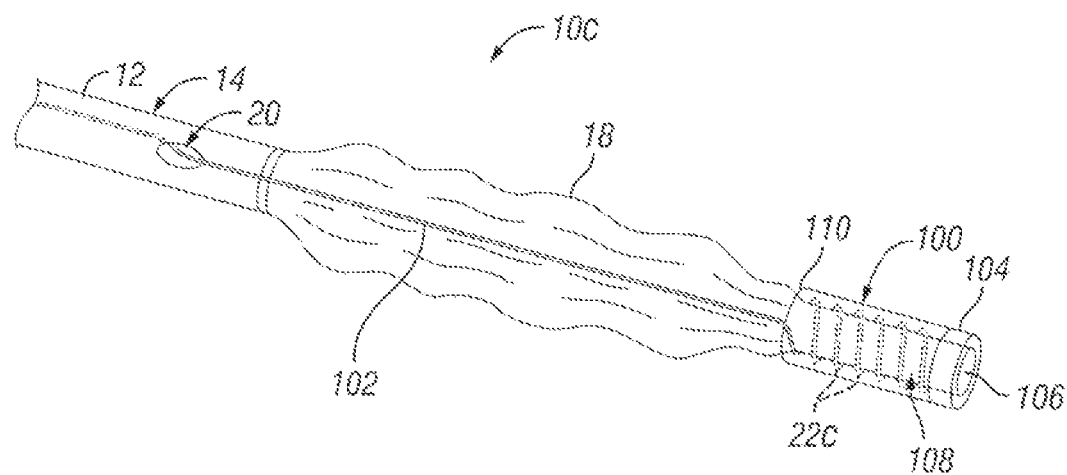
FIG. 5A is a partial perspective of another embodiment of a PTA catheter of the present invention with its cutting or scoring element in a stowed position and its balloon in a deflated configuration.

FIGS. 5A through 5D show another embodiment of the present invention. In this embodiment, the device 10c comprises an elongate catheter shaft 14 and balloon 18 substantially as described above with respect to FIGS. 1A-20. A distal portion 100 extends distal to the balloon 18. This distal portion 100 comprises a distal tube 108 having a lumen 106 that terminates in a distal end opening. The distal tube 108 may comprise a distal portion of the balloon 18. The lumen 106 may be connected to and continuous with the main lumen 26 of the catheter shaft 14 to allow passage of a guidewire and/or infusion/withdrawal of fluids. In such embodiments, it will be appreciated that the catheter shaft 14 may include a third lumen (not shown) for inflation/deflation of the balloon 18. Optionally, a radiopaque marker band 104 may be provided on the distal tip, as shown. A cutting or scoring member 22c, substantially as described above, is biased to a helical configuration and is initially disposed in a stowed position around the outer surface of the distal tube 108, as seen in FIG. 5A. A distal region of the cutting or scoring member 22c may be connected to the distal portion 100 of the device 10c. As described more fully below, in embodiments where a distal region of the cutting or scoring member 22c may be connected to the distal portion 100 of the device 10c, such connection may optionally be a releasable connection which allows an operator to disconnect the cutting or scoring member 22c from the distal portion 100 while the device 10c is inserted in a patient's body.

Figure 1B:
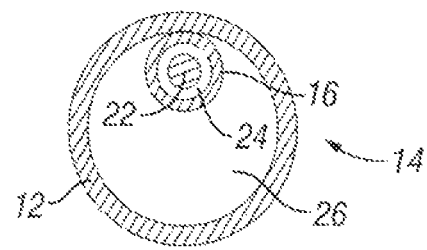
FIG. 1B is a cross-sectional view through line 1B of FIG. 1.
Figure 5B:
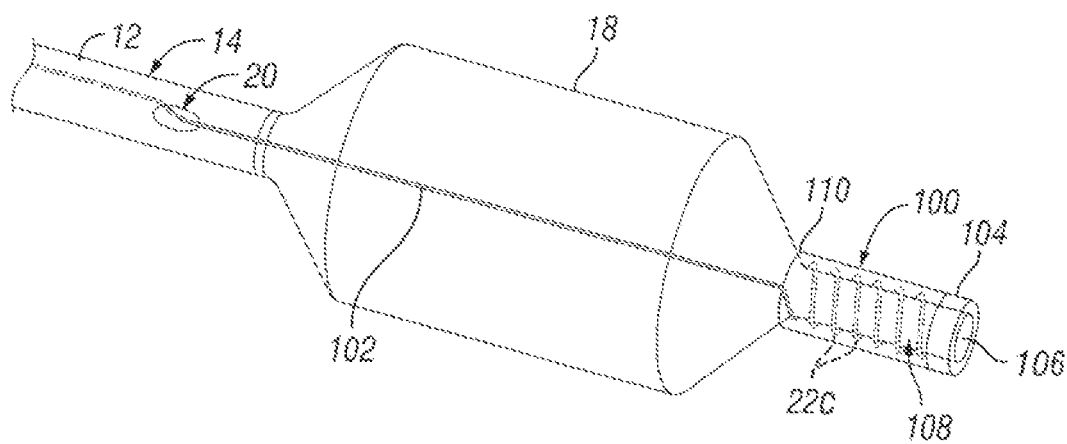
FIG. 5B shows the device of FIG. 5A with its cutting or scoring element in a stowed position and its balloon in an inflated configuration.

Optionally, an outer sheath 110 covers the distal tube 108 and stowed cutting or scoring member 22c. A pull member 102, such as a wire of filament, is attached to a proximal end of the cutting or scoring member 22c. This pull member 102 extends through opening 20 and through the second lumen 24 of the catheter shaft 14 (see FIG. 1B). The pull member 102 runs along side the deflated balloon 18, as shown. With the cutting or scoring member 22c in the stowed position, the balloon 18 may be inflated one or more times, as seen in FIG. 5B, to perform one or more balloon angioplasty dilations without cutting or scoring. The pull member 102 is preferably small in diameter and substantially smooth so as not to cause cutting or scoring of the blood vessel wall when pressed against the blood vessel wall by the expanded balloon 18.

Figure 5C:
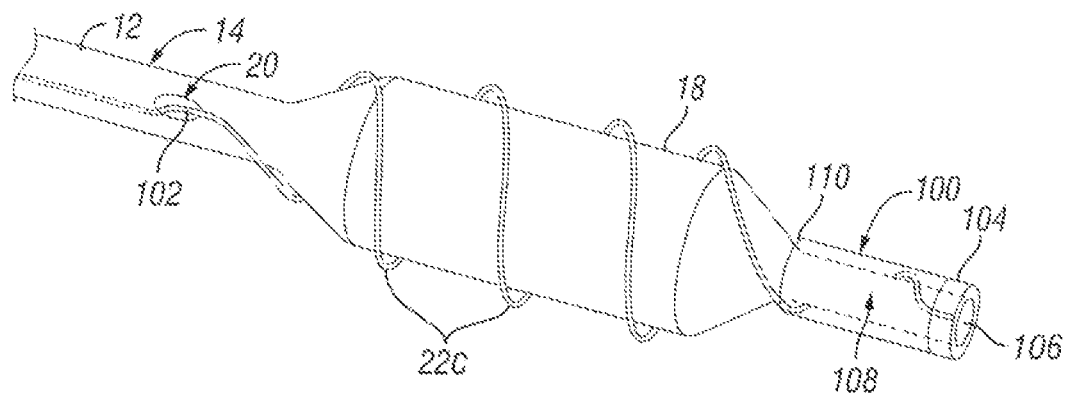
FIG. 5C shows the device of FIG. 5A with its cutting or scoring element moved to the operative position while the balloon is in a partially deflated configuration.
Figure 5D:
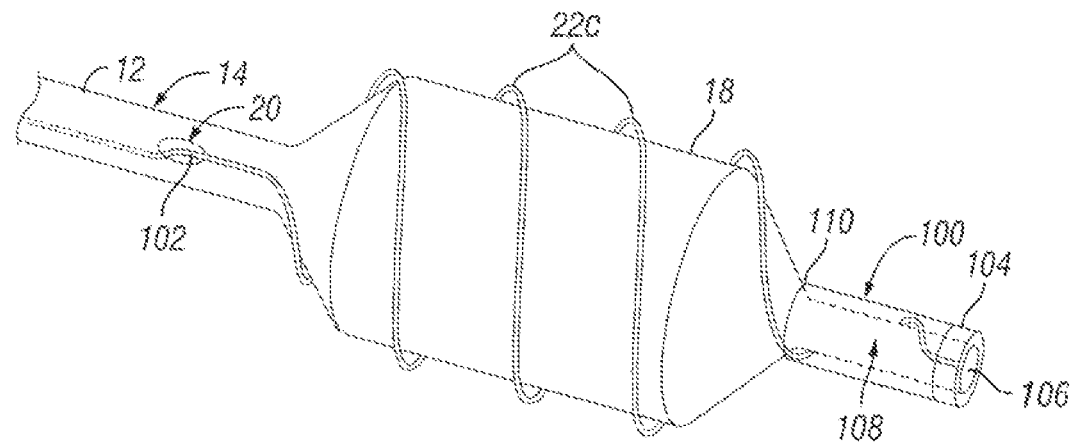
FIG. 5D shows the device of FIG. 5A with its cutting or scoring element in the operative position and its balloon in a fully inflated configuration.

If and when balloon dilation with cutting or scoring is desired, the pull member 102 may be retracted in the proximal direction so as to pull the helical cutting or scoring member 22c from the stowed position, seen in FIGS. 5A-5B, to an operative position wherein it extends in convolutions around the balloon 18. The balloon 18 may be fully or partially deflated as the cutting or scoring member 22c is moved over the outer surface of the balloon 18 and into the operative position, as shown in FIG. 5C. Once the cutting or scoring member 22c is in the operative position, the balloon 18 may be fully inflated causing the convoluted cutting or scoring member to radially expand along with the balloon 18 and resulting in cutting or scoring of the blood vessel wall as desired, as shown in FIG. 5D.

When it is subsequently desired to remove the device 10c, the balloon 18 is fully deflated and the cutting of scoring member 22c will radially contract and/or be pulled tight on the deflated balloon so that the device 10c may be withdrawn through the vasculature without causing trauma to the blood vessel walls. In some embodiments, a sheath (not shown) may be advanced over the deflated balloon 18 and radially collapsed on cutting or scoring member 22c to deter trauma to blood vessels as the device 10c is withdrawn. In other embodiments, a guide catheter may be positioned near the balloon 18 and the deflated balloon 18 and radially collapsed cutting or scoring member 22c may be retracted into the guide catheter and then removed along with the guide catheter thereby preventing the cutting or scoring member from causing trauma during withdrawal. In other embodiments, if the cutting or scoring member 22c is not attached to the distal portion 100 of the device 10c or if such attachment is releasable, the entire cutting or scoring member 22c may be retracted through opening 20 and into the catheter shaft 14 prior to removal of the device 10c. In embodiments where there is an option releasable connection between a distal portion of the cutting or scoring member 22c and the distal portion 100 of the device 10c, an operator may volitionally release such connection to allow the cutting or scoring member 22c to be fully retracted through opening 20 and into the catheter shaft 14. In such embodiments, any suitable type of frangible, severable or releasable connection may be used, such as those which are separated by introduction of pressurized fluid, melting, thermally degrading, deadhering, dissolving, rotating, mechanically releasing or otherwise. Examples of such releasable connections are found in a number of embolic coil implantation systems of the type commonly used to treat cerebral aneurysms and other vascular defects in the brain, including but not limited to those described in U.S. Pat. Nos. 5,122,136; 5,108,407; 5,350,397; 6,113,622; 6,203,547 and 7,708,755 as well as United States Patent Application Publication Nos. 2002/0165569; 2004/0034363 and 2006/0276823, the entire disclosure of each such patent and patent application being expressly incorporated herein by reference.

The present invention is based on a deployable and retrievable cutting or scoring element, which may be a metallic element, that allows for a selective scoring of the lesion, given the deployable-retrievable unique configuration of the cutting or scoring element. This accounts for the possibility to selectively deliver scoring balloons to the lesion site, having the opportunity to choose a non-scoring traditional PTA balloon configuration as an alternative. This invention allows for a dual use of the balloon object of the present invention: in fact the plaque is dilated thanks to the help of the scoring elements on the balloon and then the lesion can be easily treated with the bare balloon, completing the lesion treatment. Alternatively, the balloon is a drug coated balloon and/or the cutting or scoring member comprises a drug coating so that a suitable amount of drug can be provided at the lesion site, e.g. to avoid or at least to remarkably reduce undesired restenosis effects.

It is to be appreciated that this invention enables a single balloon catheter to be used for initial cutting or scoring of a lesion (in case it is heavily calcified or fibrotic) followed by standard balloon-alone PTA or, conversely, initial balloon-only dilation (or attempted balloon-only dilation) followed by cutting or scoring of the lesion. By using the PTA catheter devices of the present invention, physicians may elect to apply cutting or scoring treatment to a lesion only when this is believed to be strictly necessary for limiting in-vessel restenosis without the need for use of a second balloon catheter. On the other hand, after cutting or scoring of a lesion has been performed, the physician may use the same PTA catheter to deliver conventional balloon-only angioplasty, thus highly customizing the treatment configuration to patient specific needs and clinical status.

In any embodiment of the invention, the cutting or scoring member 22, 22a, 22b may be connected to a generator or other energy source to provide for active cutting or scoring in which radiofrequency, thermal or other energy is delivered to the vessel wall tissues which come into contact with the cutting or scoring member 22, 22a, 22b. Such a device may be used, for instance, for renal denervation treatments.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A device comprising:
an elongate catheter shaft;
an inflatable balloon positioned on the catheter shaft; and
a cutting or scoring member that is axially moveable relative to the catheter shaft along a longitudinal axis of the catheter shaft from a first position in which the cutting or scoring member is positioned to perform a cutting or scoring function, the cutting or scoring member comprising an elongate member that extends over the balloon when the cutting or scoring member is in the first position, to a second position in which the cutting or scoring member is not positioned to perform a cutting or scoring function,
wherein a distal portion of the cutting or scoring member is attached to a distal portion of the catheter shaft when the cutting or scoring member is in the first position, and
wherein the elongate member forms helical convolutions around the balloon when the cutting or scoring member is in the first position and the balloon is in an inflated configuration.

2. The device of claim 1, wherein the cutting or scoring member comprises a wire.

3. The device of claim 1, wherein the cutting or scoring member comprises an elastic or superelastic material.

4. The device of claim 1, wherein the cutting or scoring member assumes a substantially linear configuration when the cutting or scoring member is in the second position.

5. The device of claim 1, wherein the balloon defines an outer surface, and wherein:
when the cutting or scoring member is in the first position, the cutting or scoring member extends over the outer surface of the balloon, such that the cutting or scoring member is positioned to perform the cutting or scoring function upon inflation of the balloon when the cutting or scoring member is in the first position, and
when the cutting or scoring member is in the second position, the cutting or scoring member does not extend over at least a portion of the outer surface of the balloon, such that the cutting or scoring member is not positioned to perform the cutting or scoring function upon inflation of the balloon when the cutting or scoring member is in the second position.

6. The device of claim 1, wherein the distal portion of the cutting or scoring member is attached to the distal portion of the catheter shaft by a releasable attachment when the cutting or scoring member is in the first position, and wherein the cutting or scoring member is configured to be proximally withdrawn into a lumen of the catheter shaft when the releasable attachment is released.

7. The device of claim 1, wherein the catheter shaft defines a lumen, and wherein the cutting or scoring member is positioned within the lumen and proximal to the balloon when the cutting or scoring member is in the second position.

8. The device of claim 7, wherein the lumen comprises a first lumen, and wherein the catheter shaft further defines a second lumen configured to receive an inflation fluid for inflating or deflating the balloon.

9. The device of claim 7, wherein the cutting or scoring member is configured to assume a substantially linear configuration within the lumen when the cutting or scoring member is in the second position.

10. The device of claim 7, wherein the catheter shaft includes an outer wall that defines an opening proximal to the balloon, and wherein the cutting or scoring member is axially moveable from the first position to the second position by at least proximally withdrawing the cutting or scoring member through the opening and into the lumen of the catheter shaft.

11. The device of claim 1, wherein the cutting or scoring member is configured to deliver at least one of radiofrequency energy or thermal energy to patient tissue.

12. A device comprising:
an elongate catheter shaft defining a lumen;
an inflatable balloon positioned on the catheter shaft; and
an elongate cutting or scoring member attached to a distal portion of the catheter shaft via a releasable attachment when the cutting or scoring member is in a first position in which the cutting or scoring member extends over the balloon,
wherein the cutting or scoring member is axially moveable relative to the catheter shaft along a longitudinal axis of the catheter shaft from the first position to a second position when the releasable attachment is released, wherein the cutting or scoring member is positioned within the lumen when the cutting or scoring member is in the second position.

13. The device of claim 12, wherein the cutting or scoring member extends over the balloon by forming loops or convolutions around the balloon when the cutting or scoring member is in the first position.

14. The device of claim 12, wherein the cutting or scoring member assumes a substantially linear configuration within the lumen when the cutting or scoring member is in the second position.

15. The device of claim 12, wherein the cutting or scoring member is configured to deliver at least one of radiofrequency energy or thermal energy to patient tissue.

16. A method comprising:
advancing a device through a body lumen of a patient, the device comprising:
an elongate catheter shaft;
an inflatable balloon positioned on the catheter shaft; and
a cutting or scoring member that is axially moveable relative to the catheter shaft along a longitudinal axis of the catheter shaft from a first position in which the cutting or scoring member is positioned to perform a cutting or scoring function, the cutting or scoring member comprising an elongate member that extends over the balloon when the cutting or scoring member is in the first position, to a second position in which the cutting or scoring member is not positioned to perform a cutting or scoring function,
wherein a distal portion of the cutting or scoring member is attached to a distal portion of the catheter shaft when the cutting or scoring member is in the first position;
inflating the balloon within the body lumen while the cutting or scoring member is in the first position; and
inflating the balloon while the cutting or scoring member is in the second position to dilate the body lumen without cutting or scoring obstructive matter in the body lumen.

17. The method of claim 16, wherein the cutting or scoring member forms loops or convolutions around the balloon when the cutting or scoring member is in the first position.

18. The method of claim 16, wherein the distal portion of the cutting or scoring member is attached to the distal portion of the catheter shaft by a releasable attachment when the cutting or scoring member is in the first position, the method further comprising:
deflating the balloon;
releasing the releasable attachment of the distal portion of the cutting or scoring member from the distal portion of the catheter shaft;
positioning the cutting or scoring member in the second position by at least proximally withdrawing the cutting or scoring member into a lumen of the catheter shaft.

19. The method of claim 16, wherein the cutting or scoring member is configured to assume a substantially linear configuration when the cutting or scoring member is in the second position.

20. The method of claim 16, wherein the catheter shaft includes an outer wall that defines an opening proximal to the balloon, and wherein positioning the cutting or scoring member in the second position comprises proximally withdrawing the cutting or scoring member through the opening and into the lumen of the catheter shaft.

* * * * *